US012606530B2

(12) United States Patent
Li

(10) Patent No.: US 12,606,530 B2
(45) Date of Patent: Apr. 21, 2026

(54) ANILINE ACID ANHYDRIDE, PREPARATION METHOD THEREFOR, AND POLYAMINO ACID-GRAFTED CHAIN

(71) Applicant: SOOCHOW UNIVERSITY, Suzhou (CN)

(72) Inventor: Zhanxiong Li, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 498 days.

(21) Appl. No.: 18/028,542

(22) PCT Filed: Jan. 27, 2021

(86) PCT No.: PCT/CN2021/074017

§ 371 (c)(1),
(2) Date: Mar. 26, 2023

(87) PCT Pub. No.: WO2022/062288

PCT Pub. Date: Mar. 31, 2022

(65) Prior Publication Data

US 2023/0357171 A1 Nov. 9, 2023

(30) Foreign Application Priority Data

Sep. 28, 2020 (CN) ........................ 202011045890.X

(51) Int. Cl.

| | |
|---|---|
| ***C07D 263/44*** | (2006.01) |
| ***C08G 69/48*** | (2006.01) |
| ***D06M 14/04*** | (2006.01) |
| ***D06M 14/06*** | (2006.01) |
| ***D06M 101/06*** | (2006.01) |
| ***D06M 101/12*** | (2006.01) |

(52) U.S. Cl.

CPC ........... *C07D 263/44* (2013.01); *C08G 69/48* (2013.01); *D06M 14/04* (2013.01); *D06M 14/06* (2013.01); *D06M 2101/06* (2013.01); *D06M 2101/12* (2013.01); *D06M 2200/12* (2013.01)

(58) Field of Classification Search

CPC .. C07D 263/44; C07D 263/08; C07D 263/34; C07D 263/36; C08G 69/10; C08G 69/48; D06M 14/04; D06M 14/06; D06M 15/595; D06M 2101/06; D06M 2101/10; D06M 2101/12; D06M 2200/12

See application file for complete search history.

(56) References Cited

FOREIGN PATENT DOCUMENTS

| | | | |
|---|---|---|---|
| CN | 2010260832 | A | 11/2010 |
| CN | 105199098 | A | 12/2015 |
| CN | 110938087 | A | 3/2020 |
| CN | 112127157 | A | 12/2020 |
| CN | 112194638 | A | 1/2021 |
| CN | 112387307 | A | 2/2021 |
| CN | 112390819 | A | 2/2021 |

OTHER PUBLICATIONS

CN 110938087 A (Dec. 30, 2015) machine translation.*

* cited by examiner

*Primary Examiner* — Ana L. Woodward
(74) *Attorney, Agent, or Firm* — SZDC Law PC

(57) ABSTRACT

Disclosed are an aniline anhydride, a preparation method therefor, and a polyaminoacid graft chain. In the presence of an acid binding agent, an addition-elimination reaction is carried out between N-phenyl amino acid and Boc anhydride to obtain N-phenyl-Boc-glycine; and under a nitrogen atmosphere, the N-phenyl-Boc-glycine is subject to cyclization to obtain the aniline anhydride. The polyaminoacid graft chain can be obtained using the aniline anhydride disclosed by means of chemical grafting and thus be covalently bonded with fiber. The fastness is high, the wearability of fabric is not affected, and the problem of low fastness of water-repellent fabric obtained by coating is solved. The polyaminoacid graft chain is biocompatible, naturally degradable and environmentally friendly, and is consistent with the current trend of developing green chemicals.

4 Claims, 3 Drawing Sheets

R= $-CF_3$

ANILINE ACID ANHYDRIDE, PREPARATION METHOD THEREFOR, AND POLYAMINO ACID-GRAFTED CHAIN

This application is the National Stage Application of PCT/CN2021/074017, filed on Jan. 27, 2021, which claims priority to Chinese Patent Application No. 202011045890.X, filed on Sep. 28, 2020, which is incorporated by reference for all purposes as if fully set forth herein.

TECHNICAL FIELD

The invention relates to an aniline acid anhydride, and its preparation method and a polyamino acid graft chain, in particular to a fabric modified by polyamino acid grafting, belonging to the technical field of special functional textiles and their preparation.

BACKGROUND OF INVENTION

With the improvement of people's living standards, people's requirements for modern textiles are becoming higher and higher. Therefore, textiles are becoming more functional. For example, it's hoped that textiles can be waterproof, windproof, antibacterial, anti-ultraviolet and of other functions. In order to meet people's demand for textiles, the surfaces of some natural or man-made fibers must be modified to make textiles functional.

The prior art discloses a wear-resistant, environmentally friendly and degradable super-hydrophobic coating finishing method. The super-hydrophobic coating is constructed by a two-step dipping method. The superhydrophobicity is obtained by grafting the low surface energy substance stearic acid. The production process and equipment are extremely simple, the reaction conditions are mild, and the cost is low. At the same time, the product has excellent wear resistance, soap resistance, acid and alkali resistance. And can be directly applied to large-scale industrial production; fabrics treated by this method can obtain good hydrophobicity, oil-water separation and UV protection properties, green and environmental protection, and can be naturally degraded. Separation materials, etc. are widely used.

However, the durability of the water-accumulating function obtained by the coating treatment of the fabric is not good.

SUMMARY OF THE INVENTION

Technical Problems

The invention discloses an aniline acid anhydride, and its preparation method and a polyamino acid graft chain.

The aniline acid anhydride is used for the surface modification of fiber materials after the ring-opening polymerization. By controlling the treatment process, a surface hydrophobic modified fabric is obtained on the premise that the strength, permeability, whiteness, hand feeling and other properties of the fabric (or fiber) are not affected. In view of the unsatisfactory durability of the water-repellent fabric at present, the present invention that aniline acid anhydride forms a hydrophobic graft chain, which can provide the water-repellent function and durable water repellency.

SOLUTIONS TO THE PROBLEMS

Technical Solution

The technical scheme for realizing the purpose of the invention is: The aniline acid anhydride, which the chemical structural formula is as follows:

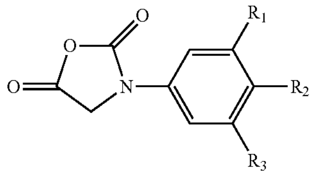

Wherein: $R_1$, $R_2$, $R_3$ are independently selected from H, $—CH_3$, $—CH_2CH_3$ or $—CF_3$; $R_4$ is $—CH_3$ or $—CH_2CH_3$.

The polyamino acid-grafted chain, which the chemical structural formula is as follows:

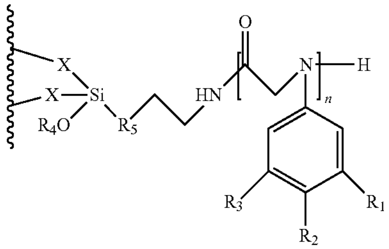

Wherein: $R_1$, $R_2$, $R_3$ are independently selected from H, $—CH_3$, $—CH_2CH_3$ or $—CF_3$; $R_4$ is $—CH_3$ or $—CH_2CH_3$; $R_5$ is $—CH_2—$ or $—CH_2CH_2CH_2NH—$; X is 0 or NH: n=3~200.* Indicates end-capping group or a substrate, such as fabric, the polyamino acid-grafted chain of the present invention is not only exists on the substrate to water-repellent, but also prepared independently and then applied to the substrate finishing.

The preparation method of the aniline acid anhydride above, which includes the following steps, N-phenyl amino acid reacts with Boc anhydride in the presence of acid-binding agent for the addition-elimination reaction to obtain N-phenyl-tert-butyloxycarboxyglycine; N-phenyl-tert-butyloxycarboxyglycine is subject to the cyclization reaction under nitrogen protection to obtain aniline acid anhydride.

The preparation method of the polyamino acid-grafted chain, which includes the following steps, N-phenyl amino acid reacts with Boc anhydride in the presence of acid-binding agent to obtain N-phenyl-tert-butyloxycarboxyglycine; N-phenyl-tert-butyloxycarboxyglycine is subject to the cyclization reaction under nitrogen protection to obtain aniline acid anhydride; mixing terminal amino substance and anilino acid anhydride to obtain the polyamino acid-grafted modified water-repellent fabric.

In the present invention, the N-phenyl-tert-butyloxycarboxyglycine is as follows:

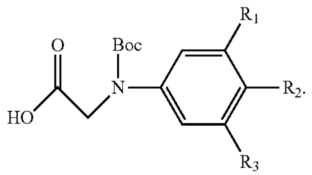

In the present invention, when preparing polyamino acid-grafted chain from aniline acid anhydride through ring-opening polymerization, the temperature is 0~80° C., the best temperature is 70° C., the time is 1~120 h, and the best time ranges from 24 to 60 h; Preferably, the reaction temperature is a four-step temperature increase, such as room temperature+(30~50° C.)+(50~60° C.)+(60~70° C.), the difference between adjacent steps temperature is 5~25° C.

The invention discloses the application of the aniline acid anhydride in the preparation of water-repellent polyamino acid-grafted chain, or applied in the preparation of water-repellent finishing agent.

In the present invention, the terminal amino substance is an amino silane coupling agent or things treated with amino silane coupling agent, such as a fabric treated with amino silane coupling agent. The amino silane coupling agent is hydrolyzed in the mixed solvent of water/ethanol to obtain the hydrolysate, and the fabric is put into the hydrolysate for reaction to obtain the pretreated fabric with amino groups on the surface of fiber, which is the amino-pretreated fabric; the amino silane coupling agent is any of aminopropyltriethoxysilane, aminopropyltrimethoxysilane, aminoethylaminopropyltriethoxysilane, and aminoethylaminopropyltrimethoxysilane.

In the present invention, N-phenyl-tert-butyloxycarboxyglycine is subject to the cyclization reaction under nitrogen protection to obtain aniline acid anhydride; Specifically, N-phenyl-tert-butyloxycarbonylglycine is dissolved in anhydrous solvent, a cyclizing agent is added under the nitrogen protection, and then the cyclization reaction is carried out to generate aniline acid anhydride; the cyclizing agent is $PCl_3$; the anhydrous solvent is anhydrous dichloromethane, anhydrous trichloromethane or anhydrous tetrachloroethane; it is preferred to add cyclizing agent in 2~10 batches, preferably in 3~5 batches; the temperature of adding cyclizing agent is −20~45° C., preferably −5~5° C.; the temperature of cyclization reaction is 5~45° C., preferably 20~30° C.; the time is 0.1 to 48 hours, preferably 12 to 24 hours.

In the present invention, N-phenyl amino acid reacts with Boc anhydride in the presence of acid-binding agent to obtain N-phenyl-tert-butyloxycarboxyglycine; the acid-binding agent is triethylamine or pyridine; the reaction temperature is 5~45° C. and the time is 0.1~24 h. Furthermore, the molar ratio of N-phenyl amino acid to Boc anhydride is 1:2.5. Preferably, the Boc anhydride solution is added dropwise to the mixture of N-phenyl amino acid solution and acid-binding agent for the addition-elimination reaction to obtain N-phenyl-N-tert-butyloxycarbonyl glycine; the adding time of Boc anhydride solution is 20~120 min, preferably 30~60 min. In N-phenyl amino acid solution, the solvent is water/1,4-dioxane, and the volume ratio of water and dioxane is 1:1~2, preferably 1:1~1.5; in Boc acid anhydride solution, the solvent is any of 1,4-dioxane, tetrahydrofuran or ether. The reaction temperature of N-phenyl amino acid with Boc acid anhydride is 5~45° C., preferably room temperature; the reaction time is 0.1~24 h, preferably 12~18 h.

BENEFICIAL EFFECTS OF THE INVENTION

Beneficial Effects

Compared with the prior art, the beneficial effects of the technical scheme provided by the invention are: the present invention discloses for the first time anilino acid anhydride, especially when the water-repellent fabric modified by the polyamino acid grafting it is connected with the fiber through covalent bond, thus endowing the hydrophobic fabric with excellent durability and fastness, solving the problem of poor fastness caused by the physical effect of conventional coating on the fabric, as well as the problems of high cost and strict equipment requirements of other physical modifications. The polyamino acid prepared in the present invention is an environmentally friendly polymer that has excellent biocompatibility and is naturally degradable, complying with the current trend of developing green textiles.

BRIEF DESCRIPTION OF ATTACHED DRAWINGS

Figure 1:
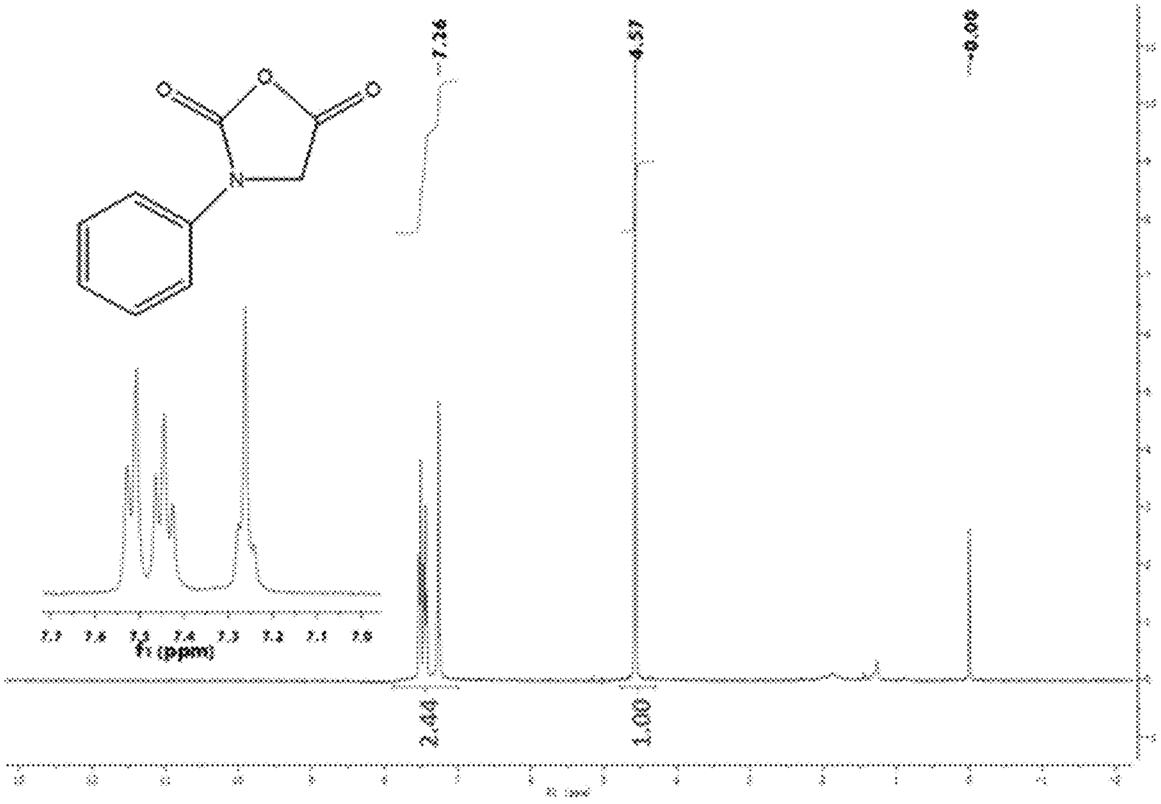
FIG. 1 is the HNMR image of N-aniline acid anhydride prepared in Example 2, and the solvent is Chloroform-d.

The present invention discloses the preparation method of the aniline acid anhydride, including the following steps.

Addition-elimination reaction: N-phenyl amino acid undergoes addition-elimination reaction with Boc acid anhydride in mixed solvent to form the intermediate N-phenyl-tert-butyloxycarbonyglycine.

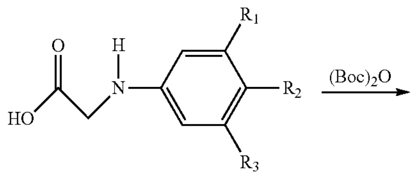

-continued

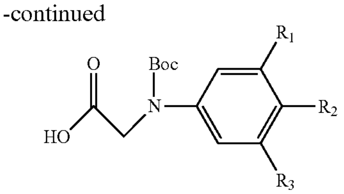

$PCl_3$ cyclization: N-phenyl-tert-butyloxycarbonylglycine is cyclized by carbonyl group and Boc group under the action of the cyclizing agent $PCl_3$ to form N-aniline acid anhydride.

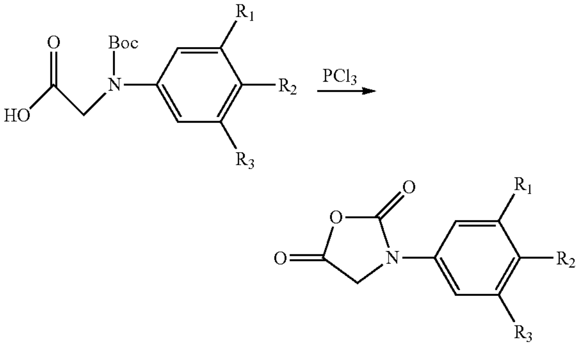

Further, polyamino acid graft chains are prepared by the polymerization of aniline acid anhydrides. Taking the fabric treated with aminosilane coupling agent as an example, on the surface of the fibers, the ring-opening polymerization of N-aniline acid anhydride monomer is induced on the surface of the fiber to form graft chain.

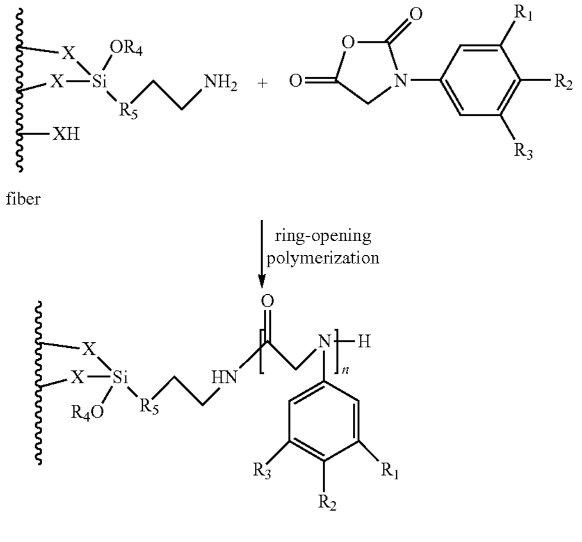

Wherein, $R_1$, $R_2$, $R_3$=H, $-CH_3$, $-CH_2CH_3$ or $-CF_3$.

$R_4$=$-CH_3$ or $-CH_2CH_3$.

$R_5$=$-CH_2-$ or $-CH_2CH_2CH_2NH-$.

X=-0- or —NH—.

n=3~200.

The raw materials involved in the present invention are commercially available conventional products, and the specific preparation method and test operation are conventional methods. Unless otherwise specified, they are carried out at room temperature and conventional environment. The fabrics used for amino pretreatment are conventional fabrics, untreated and hydrophilic.

With reference to the accompanying drawings and Example, the technical scheme of the present invention will be described in detail.

Fabric pretreatment: The amino silane coupling agent aminopropyltriethoxysilane was dissolved in the mixed solution of water/ethanol (the volume ratio of water and ethanol was 1:9), the pH of the solution was adjusted to 10 with 10% ammonia, and the transparent hydrolysate of the amino silane coupling agent was obtained by hydrolysis at room temperature for 3 h, and then a 300 g round cotton fabric was subjected to water bath reaction in the above-mentioned 400 mL amino silane coupling agent hydrolysate (the amount of the amino silane coupling agent is 6% of the weight of the fabric) with the water bath temperature of 50° C. and the reaction time of 120 min. After the reaction was completed, the fabric was taken out, washed three times, dried at 60° C. and baked at 120° C. for 3 min to obtain the pretreated cotton fabric.

The above-mentioned cotton fabric was replaced with a hemp fabric or a mulberry silk fabric, and the rest remain to obtain a hemp fabric pretreated with an aminosilane coupling agent or a silk fabric pretreated with an aminosilane coupling agent.

EXAMPLES OF THE INVENTION

Examples of the Present Invention

Example 1

(1) Synthetize N-trifluorophenyl-N-tert-butyloxycarbonyl glycine: 2500 mL single neck flask with magnetic stirrer. 52 g of N-(Trifluoromethyl) phenylglycine was taken to dissolve in the mixed solution of 800 mL of water/1,4-dioxane (the volume ratio of water and dioxane is 1:1) until it was completely transparent, then 184 mL of triethylamine solution was added with a syringe, and 400 mL of 1,4-dioxane solution containing 142 g of Boc acid anhydride was added dropwise for 40 min. The reaction happened after stirring at room temperature for 16 h, extract twice with 500 mL of n-hexane, add 800 mL of 1 N HCl solution to make it acidic, and then extract the product with 2×300 mL of ethyl acetate solution. Combined with organic phase, the organic layer was washed with 800 mL saline, washed with deionized water three times, dried with anhydrous magnesium sulfate, filtered, and distilled under reduced pressure to remove the solvent and obtain 45.3 g black-brown viscous product with a yield of 61.1%.

(2) Synthetize N-Trifluoromethyl aniline acid anhydride: Under nitrogen atmosphere, the product from above (1) was dissolved in 900 mL of anhydrous dichloromethane, the solution was cooled to 0° C. in a low-temperature reactor, and 46.0 g of $PCl_3$ solution was added into the reaction solution in three batches (16 g+15 g+15 g) through a syringe, with an interval of 15 min. The reaction solution was stirred at 0° C. for 1 h, and then transferred to room temperature for reaction for 15 hours. The solvent was removed in vacuum, and the obtained solid was dissolved in 300 mL of anhydrous dichloromethane, filtered, and the filtrate was evaporated to obtain about 23.3 g of light yellow crude product solid, with a yield of 69%. 23.0 g of light yellow solid was recrystallized in the mixed solution of anhydrous dichloromethane/n-hexane, and finally 12.9 g of white solid product (p-trifluorophenyl) aniline acid anhydride for polymerization was obtained, with a yield of 49.1%.

Example 2

(1) Synthetize N-phenyl-N-tert-butyloxycarbonyl glycine: 2500 mL single neck flask with magnetic stirrer. 40 g of N-phenylglycine was taken to dissolve in the mixed solution of 800 mL of water/1,4-dioxane (the volume ratio of water and dioxane is 1:1) until it was completely transparent, then 184 mL of triethylamine solution was added with a syringe, and 400 mL of 1,4-dioxane solution containing 142 g of Boc acid anhydride was added dropwise for 40 min. The reaction happened after stirring at room temperature for 16 h, extract the solvent twice with 500 mL of n-hexane, add 800 mL of 1 N HCl solution to make it acidic, and then extract the product with 2×300 mL of ethyl acetate solution. Combined with organic phase, the organic layer was washed with 800 mL saline, washed with deionized water three times, dried with anhydrous magnesium sulfate, filtered, and distilled under reduced pressure to remove the solvent and obtain 42.4 g black-brown viscous product with a yield of 64.3%.

Figure 2:
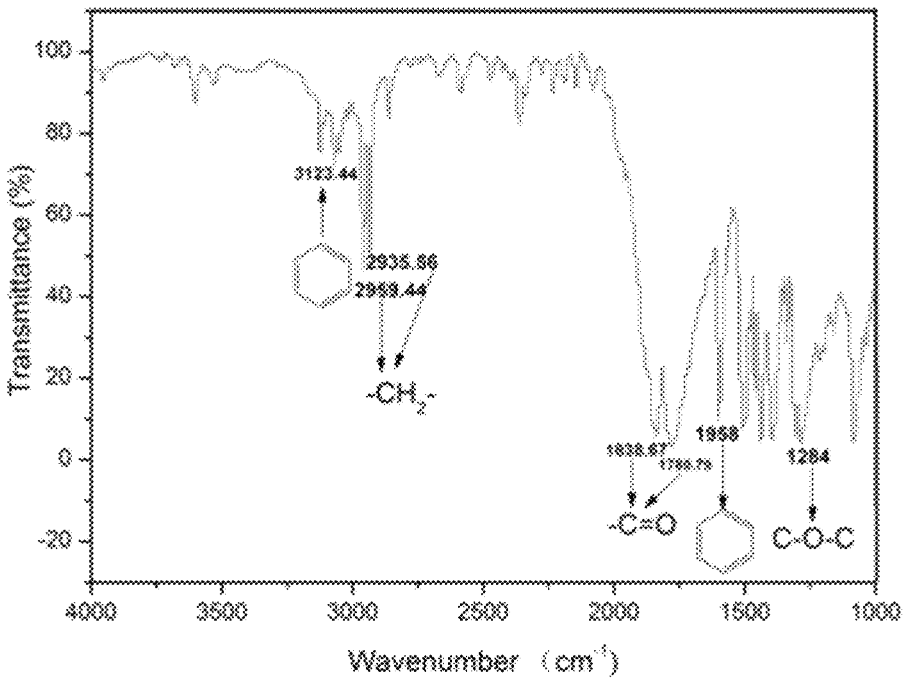
FIG. 2 is the infrared image of N-aniline acid anhydride prepared in Example 2.

(2) Synthetize N-aniline acid anhydride: Under nitrogen atmosphere, the product from above (1) was dissolved in 900 mL of anhydrous trichloromethane, the solution was cooled to 0° C. in a low-temperature reactor, and 46.0 g of $PCl_3$ solution was added into the reaction solution in three batches (16 g+15 g+15 g) through a syringe, with an interval of 15 min. The reaction solution was stirred at 0° C. for 1 h, and then transferred to room temperature for reaction for 16 hours. The solvent was removed in vacuum, and the obtained solid was dissolved in 300 mL of anhydrous dichloromethane, filtered, and the filtrate was evaporated to obtain about 21.0 g of light yellow crude product solid, with a yield of 70%. 21.0 g of light yellow solid was recrystallized in the mixed solution of anhydrous trichloromethane/n-hexane, and finally 10.1 g of white solid product for polymerization was obtained, with a yield of 47.6%. See FIG. 1 for the nuclear magnetic image and FIG. 2 for the infrared image.

Example 3

Figure 3:
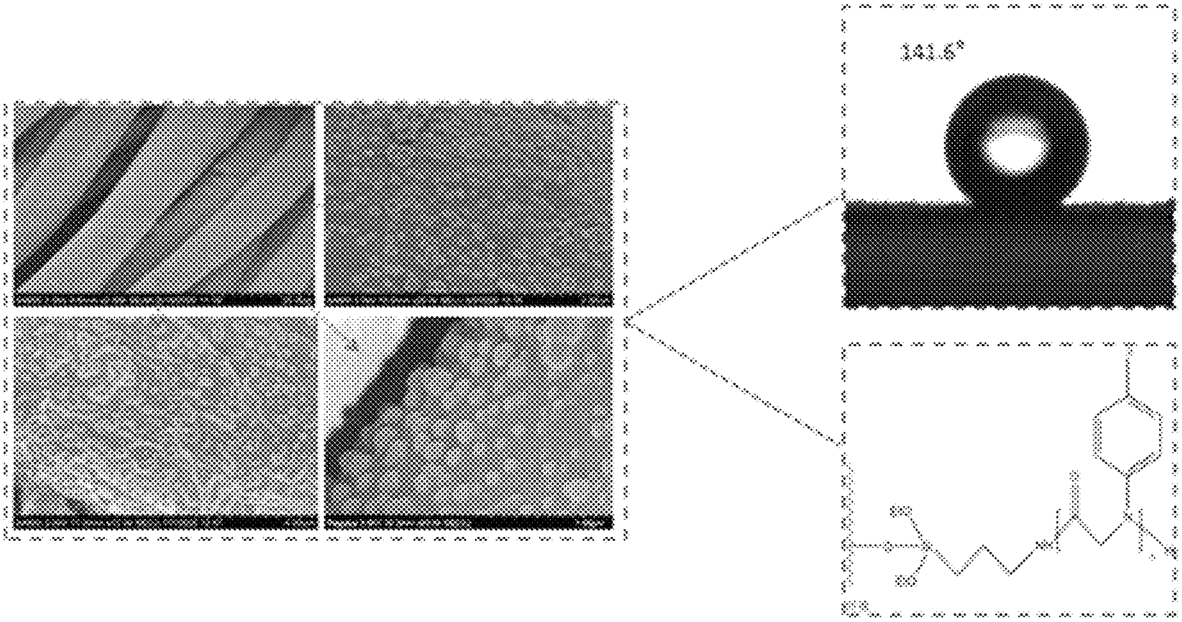
FIG. 3 is the scanning electron microscope (SEM) image (left) of the grafted modified cotton fabric through ring-opening polymerization on the fiber surface by the N-(p-trifluorophenyl) aniline acid anhydride prepared in Example 3 after soaping; the contact angle test figure (upper right) after soaping shows that the contact angle of the fabric to water is 141.6°, and the treated fabric has excellent hydrophobicity, stable soap-washing surface coating and good durability.

3.1 g of the white solid product N-trifluoromethyl aniline acid anhydride in Example 1 was taken and completely dissolved in 450 mL of N, N-dimethyl formamide (DMF) solution. And the pretreated fabric was added into the DMF solution for reaction at room temperature for 4 h. Then it was heated to 50° C. for reaction for 8 h, then to 60° C. for reaction for 12 h, finally to 70° C. for reaction for 12 h, and the total grafting reaction time was 48 h. After the reaction was completed, the fabric was taken out to terminate the reaction, washed three times, cleaned by conventional ultrasonic for 15 min, and then dried at 60° C. to obtain water-repellent cotton fabric. The structure diagram is shown in FIG. 3. The graft chain structure on the fiber surface is as follows (wavy line is fiber, n is 20~60).

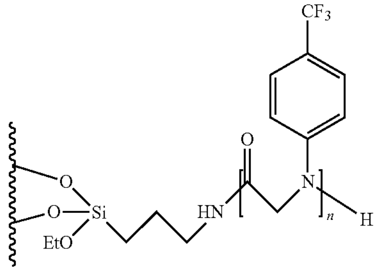

Example 4

Figure 4:
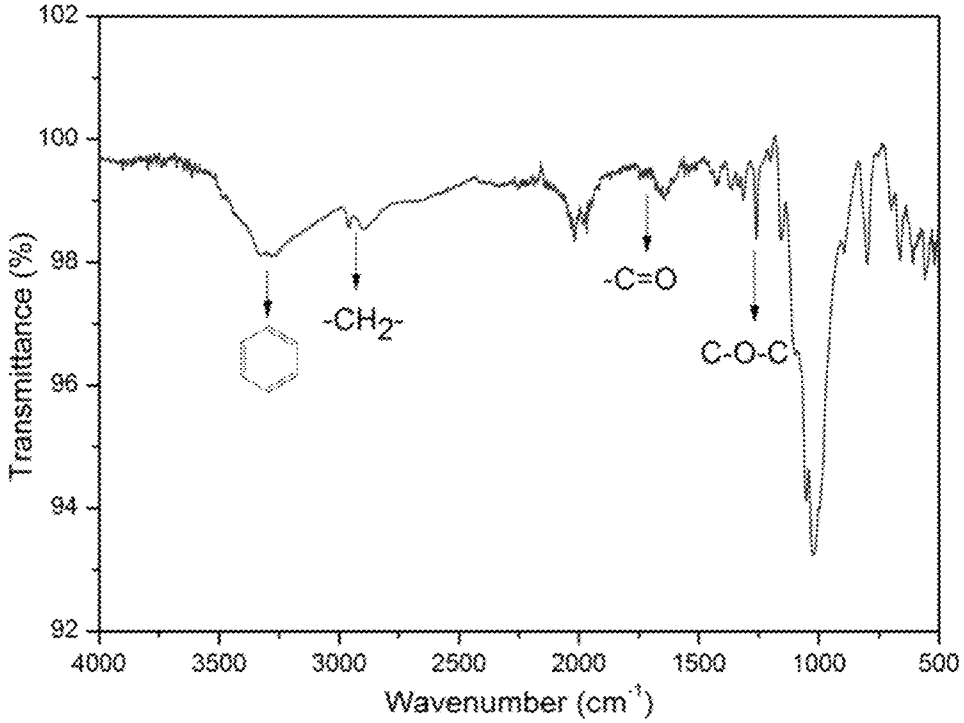
FIG. 4 is the FT-IR image of the polyphenyl amino acid grafted modified fabric prepared in Example 4. From the absorption peaks of the benzene ring and amino acid structure characteristics in the infrared absorption curve, it can be seen that the polyphenyl amino acid has been successfully grafted to the surface of linen fiber.

3.1 g of the white solid product N-aniline acid anhydride in Example 2 was taken and completely dissolved in 450 mL of N, N-dimethyl formamide (DMF) solution. And the pretreated fabric was added into the DMF solution for reaction at room temperature for 4 h. Then it was heated to 50° C. for reaction for 8 h, then to 60° C. for reaction for 12 h, finally to 70° C. for reaction for 12 h, and the total grafting reaction time was 48 h. After the reaction was completed, the linen fabric was taken out to terminate the reaction, washed three times, cleaned by conventional ultrasonic for 15 min, and then dried at 60° C. to obtain water-repellent linen fabric. The infrared spectrum of the tested fabric surface is shown in FIG. 4, where 3134.44 $cm^{-1}$ is the absorption peak of C—H stretching vibration on the phenyl substituent group, 2935.56 and 2959.44 $cm^{-1}$ correspond to the absorption peaks of $—CH_2—$, 1838.67 and 1780.79 $cm^{-1}$ are the absorption peaks when amino acid=0, and 1958 $cm^{-1}$ is the characteristic absorption peak of the structure of benzene ring. The infrared test indicates that the graft chain of phenyl polyamino acid has formed on the fiber surface. The graft chain structure on the surface of the modified fiber is as follows (wavy line is fiber, n is 50~90).

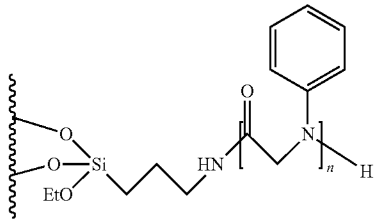

Example 5

0.25 g of the N-aniline acid anhydride (prepared in Example 2) was taken and dissolved in 45 mL tetrahydrofuran (THF), and the silk fabric pretreated with aminopropyltriethoxysilane was added to the THF solution for reaction at room temperature for 2 h. Then it was heated to 30° C. for reaction for 4 h, then to 50° C. for reaction for 12 h, finally to 60° C. for reaction for 12 h, and the total grafting reaction time was 24 h. After the reaction was completed, the fabric was taken out to terminate the reaction, washed three times, cleaned by conventional ultrasonic for 15 min, and then dried at 60° C. to obtain water-repellent silk fabric. The graft chain structure of polyamino acid on the surface of the fiber is as follows (wavy line is fiber, n is 30~70).

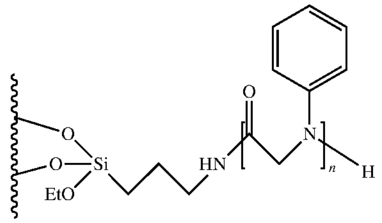

Performance test: Soaping fastness test: After the treated fabric was soaped in accordance with GB/T 3921-2008 Textiles—Tests for colour fastness—Colour fastness to washing with soap or soap and soda, the grafted modified silk fabric was tested for soaping durability.

Figure 5:
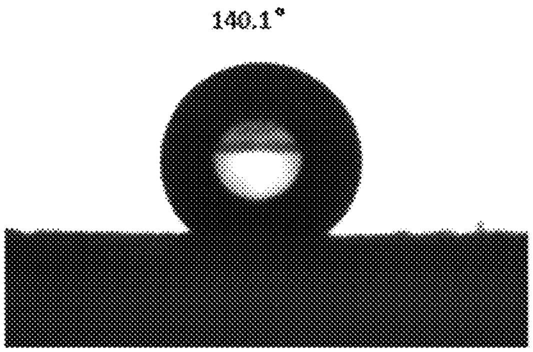
FIG. 5 is the contact angle test image of the treated fabric through ring-opening polymerization on the fiber surface by the N-aniline acid anhydride prepared in Example 4 after soaping; it's known the contact angle of the fabric to water is 140.1°, and the treated fabric has excellent hydrophobicity, stable soap-washing surface coating and good durability.
Figure 6:
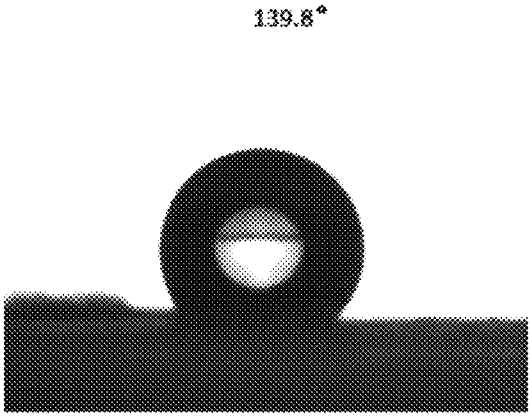
FIG. 6 is the contact angle test image of the treated fabric through ring-opening polymerization on the silk fabric surface by the N-aniline acid anhydride prepared in Example 5 after soaping; it's tested the contact angle of the fabric to water is 139.8°, and the treated silk fabric has excellent hydrophobicity.

Contact angle test: DSA100 Automatic Microscopic Droplet Wettability Tester from German Kruss was used to test the wettability of coated fabric before and after the soaping. Water was selected as the test droplet, and the volume of the droplet was 5 μL and the average of five tests was taken. The contact angles of acid anhydride on the finished fabric surface by the ring-opening polymerization before and after soaping in Example 3 were 145.4° and 141.6°, respectively. See FIG. 3 the hydrophobic property of the finished fabric was still available after soaping, indicating that the finishing durability was good. The contact angles of acid anhydride on the finished fabric surface by the ring-opening polymerization before and after soaping in Example 4 were 141.2° and 140.1°, respectively. The hydrophobic property of the finished fabric was still available after soaping as shown in FIG. 5, indicating that the finishing durability was good. The N-aniline acid anhydride in Example 4 was replaced with N-trifluoromethyl aniline acid anhydride anhydride, and the rest remained unchanged. The surface contact angles of water-repellent linen fabric before and after soaping were 141.9° and 139.3°, respectively. The contact angles of acid anhydride on the finished fabric surface by the ring-opening polymerization before and after soaping in Example 5 were 142.7° and 139.8°, respectively. The hydrophobic property of the finished fabric was still available after soaping as shown in FIG. 6, indicating that the finishing durability was good.

Degradability test: The sample of water-repellent fabric was cut into round fabrics with a diameter of about 10 mm, washed with ethanol and deionized water sequentially, and then dried in vacuum for 24 hours at 37° C. for standby. Papain was used as proteolytic enzyme. The protease was activated in 0.01M cysteine, 0.04M EDTA buffer solution (pH 8.0), and the concentration was 1 mg enzyme/ml solution. A pipette was used to remove 3 mL of enzyme solution and added into the corresponding orifice of the culture plate. Then the round fabric was weighed and placed into the orifice of the culture plate to ensure that the sample was completely immersed in the enzyme solution. After degradation for a certain time, samples were taken out and cleaned with a large amount of deionized water, then vacuum dried at 37° C. for 24 h, and weighed and recorded.

The calculating formula of weight loss rate is as follows.

$$\text{Mass loss (\%)} = \frac{W_0 - W_i}{W_0} \quad (1)$$

Wherein: $W_o$ is the mass of the fabric before degradation, $W_i$ is the mass after degradation.

Figure 7:
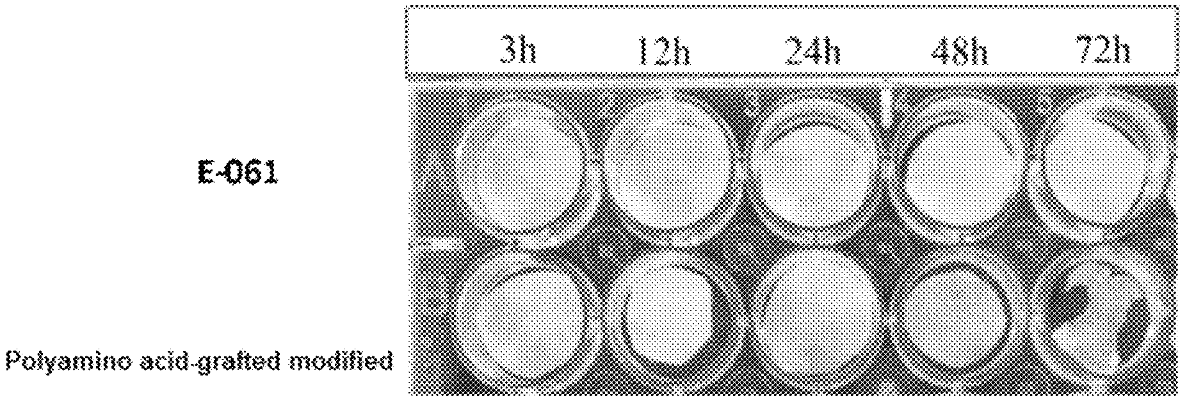
FIG. 7 is an optical photo of the polyamino acid-grafted modified silk fabric prepared in Example 5 and the silk fabric finished with commercially available water-repellent finishing agent after degradation catalyzed by protease and it can be seen that the polyamino acid-grafted modified silk fabric is easy to be degraded, while the silk fabric finished with the commercially available water-repellent finishing agent is basically not degraded under this condition.

The mass residual rate of the water-repellent fabric was 30.3% after 72 h degradation in Example 3. The mass residual rate of the water-repellent fabric was 38.1% after 72 h degradation in Example 4. The mass residual rate of the water-repellent fabric was 22.8% after 72 h degradation in Example 5. See FIG. 7 which is a schematic diagram of the downward flow.

Controls 1

(1) Preparation of water-repellent silk fabric: The fluorine-containing water-repellant finishing agent E-061, purchased from 3M Company, was diluted into a finishing solution with a mass concentration of 30 g/L with deionized water. The mulberry silk fabric was moistened with distilled water and put into the finishing solution (bath ratio 1:20), and soaked for 15 min.

Finishing process flow: two soakings and two rollings (rolling rate: 80%)→pre-baking (90° C., 3 min)→baking (155° C., 2 min)→finishing silk fabric.

(2) Soaping fastness test: After the treated fabric was soaped in accordance with GB/T 3921-2008 Textiles—Tests for colour fastness—Colour fastness to washing with soap or soap and soda, the grafted modified silk fabric was tested for soaping durability.

(3) Contact angle test: DSA100 Automatic Microscopic Droplet Wettability Tester from German Kruss was used to test the wettability of coated fabric before and after the soaping. Water was selected as the test droplet, and the volume of the droplet was 5 μL and the average of five tests was taken. The contact angles of acid anhydride on the finished fabric surface before and after soaping were 136.8° and 108.1°, respectively. After soaping, the contact angle decreased a lot, the hydrophobic property decreased, and the finishing durability was poor.

(4) Degradability test: The sample of water-repellent fabric was cut into round fabrics with a diameter of about 10 mm, washed with ethanol and deionized water sequentially, and then dried in vacuum for 24 hours at 37° C. for standby. Papain was used as proteolytic enzyme. The protease was activated in 0.01M cysteine, 0.04M EDTA buffer solution (PH 8.0), and the concentration was 1 mg enzyme/ml solution. A pipette was used to remove 3 mL of enzyme solution and added into the corresponding orifice of the culture plate. Then the round fabric was weighed and placed into the orifice of the culture plate to ensure that the sample was completely immersed in the enzyme solution. After degradation for a certain time, samples were taken out and cleaned with a large amount of deionized water, then vacuum dried at 37° C. for 24 h, and weighed and recorded.

The calculating formula of weight loss rate is as follows.

$$\text{Mass loss (\%)} = \frac{W_0 - W_i}{W_0} \quad (1)$$

Wherein: $W_o$ is the mass of the fabric before degradation, $W_i$ is the mass after degradation.

The mass residual rate of the water-repellent silk fabric was 98.1% after 72 h degradation. See FIG. 7 for the top image.

The mass residual rate of the untreated mulberry silk fabric was 16.1% after 72 h degradation.

When the above mulberry silk fabric was replaced with silk fabric pretreated with aminopropyltriethoxysilane and the rest remained unchanged, the contact angles of acid anhydride on the finished fabric surface of the silk fabric treated with E-061 before and after soaping were 137.3° and 106.5°, respectively. After soaping, the contact angle decreased a lot, the hydrophobic property decreased, and the finishing durability was poor.

Controls 2

On the basis of Example 4, the condition of reaction time of 4 h at room temperature, 8 h at 50° C., 12 h at 60° C., and 12 h at 70° C., and the total grafting reaction time of 48 h was replaced by 48 h at room temperature; and the rest remained unchanged, the water contact angles on the surface of the water-repellent linen fabric before and after soap washing were 134.7° and 130.5°, respectively.

On the basis of Example 4, the condition of reaction time of 4 h at room temperature, 8 h at 50° C., 12 h at 60° C., and 12 h at 70° C., and the total grafting reaction time of 48 h was replaced by 48 h at 60° C.; and the rest remained unchanged, the water contact angles on the surface of the water-repellent linen fabric before and after soap washing were 130.9° and 122.3°, respectively.

The present invention discloses for the first time anilino acid anhydride, can initiate and induce the ring-opening polymerization of aniline-containing acid anhydride on the surface of the pretreated fiber to form a graft chain, and has good water repellency, especially excellent washing durability and degradability. The existing ring-opening polymerization method for grafting modification of material surface is mainly about the grafting modification of the surfaces of silicon-based materials or metal materials. There are few literature reports on the research of using ring-opening polymerization method to obtain modification and functionality on the fiber surface. The ring-opening polymerization of the present invention changes from a ring compound monomer to a linear polymer through ring-opening reaction, and the reaction conditions are relatively mild; the side reaction is less than the polycondensation reaction, and it is easy to obtain the high molecular weight polymer, and the ring-opening polymerization does not release as much energy as the addition reaction. The thermal effect of the polymerization process is caused by the change of the ring tension, which can control the chemical composition of the surface of the base material to obtain the modification and functionality.

The invention claimed is:

1. A polyamino acid-grafted chain, comprising the following chemical structural formula:

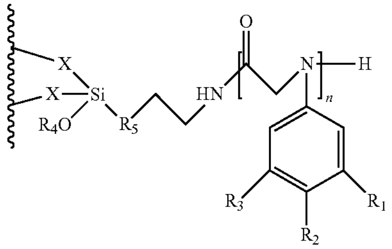

wherein: $R_1$, $R_2$, $R_3$ are independently selected from the group consisting of H, $—CH_3$, $—CH_2CH_3$ and $—CF_3$; $R_4$ is $—CH_3$ or $—CH_2CH_3$; $R_5$ is $—CH_2—$ or $—CH_2CH_2CH_2$; X is O or NH; n=3~200.

2. A method of preparing the polyamino acid-grafted chain according to the claim 1, comprising the following steps:

reacting an N-phenyl amino acid with a tert-butyloxycarbony anhydride in the presence of an acid-binding agent to obtain an N-phenyl-tert-butyloxycarboxyglycine;

subjecting the N-phenyl-tert-butyloxycarboxyglycine to a cyclization reaction under nitrogen protection to obtain an aniline acid anhydride;

mixing a terminal amino substance and the aniline acid anhydride to obtain the polyamino acid-grafted chain;

wherein the N-phenyl-tert-butyloxycarboxyglycine is:

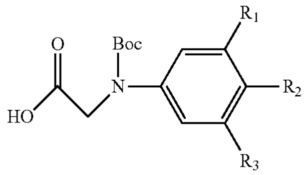

and Boc is tert-butyloxycarbonyl; and wherein: $R_1$, $R_2$, $R_3$ are independently selected from the group consisting of H, $—CH_3$, $—CH_2CH_3$ and $—CF_3$; $R_4$ is $—CH_3$ or $—CH_2CH_3$.

3. The method of preparing the polyamino acid-grafted chain according to the claim 2, wherein: a reaction temperature of is 0~80° C., and the time is 1~120 h; the terminal amino substance is an amino silane coupling agent or a fabric treated with amino silane coupling agent.

4. The method of preparing the polyamino acid-grafted chain according to the claim 3, wherein: the reaction temperature comprises a four-step temperature increase.

* * * * *